: US 9,192,473 B2
(45) Date of Patent: Nov. 24, 2015

(12) United States Patent
Hoffman et al.

(54) VALVE FRAME

(71) Applicants: Grant T. Hoffman, Bloomington, IN (US); Sean D. Chambers, Bloomington, IN (US); Ram H. Paul, Bloomington, IN (US)

(72) Inventors: Grant T. Hoffman, Bloomington, IN (US); Sean D. Chambers, Bloomington, IN (US); Ram H. Paul, Bloomington, IN (US)

(73) Assignee: COOK MEDICAL TECHNOLOGIES LLC, Bloomington, IN (US)

(*) Notice: Subject to any disclaimer, the term of this patent is extended or adjusted under 35 U.S.C. 154(b) by 185 days.

(21) Appl. No.: 13/681,362

(22) Filed: Nov. 19, 2012

(65) Prior Publication Data

US 2013/0079867 A1   Mar. 28, 2013

Related U.S. Application Data

(63) Continuation of application No. 12/273,168, filed on Nov. 18, 2008, now Pat. No. 8,313,526.

(60) Provisional application No. 60/988,987, filed on Nov. 19, 2007.

(51) Int. Cl.
*A61F 2/24* (2006.01)

(52) U.S. Cl.
CPC .............. *A61F 2/2475* (2013.01); *A61F 2/2418* (2013.01); *A61F 2/24* (2013.01); *A61F 2220/005* (2013.01); *A61F 2220/0008* (2013.01); *A61F 2220/0016* (2013.01); *A61F 2220/0058* (2013.01)

(58) Field of Classification Search
CPC ....... A61F 2/24; A61F 2/2409; A61F 2/2475; A61F 2/2418

USPC ................. 623/1.24, 2.15, 2.16, 2.17, 2.18
See application file for complete search history.

(56) References Cited

U.S. PATENT DOCUMENTS

| 5,957,949 | A | 9/1999 | Leonhardt et al. |
| 6,299,637 | B1 | 10/2001 | Shaolian et al. |
| 6,695,878 | B2 * | 2/2004 | McGuckin, Jr. . A61B 17/12109 606/153 |
| 7,070,616 | B2 | 7/2006 | Majercak et al. |
| 7,261,732 | B2 | 8/2007 | Justino |
| 7,351,256 | B2 * | 4/2008 | Hojeibane ............. A61F 2/2418 623/1.24 |
| 7,503,928 | B2 * | 3/2009 | Case .................... A61F 2/2418 623/1.24 |

(Continued)

FOREIGN PATENT DOCUMENTS

WO   WO2007047945   4/2007

OTHER PUBLICATIONS

PCT International Search Report for Application No. PCT/US2008/083870, Feb. 18, 2009.

(Continued)

*Primary Examiner* — Thomas J Sweet
*Assistant Examiner* — Seema Mathew
(74) *Attorney, Agent, or Firm* — Buchanan Nipper

(57) ABSTRACT

The disclosure relates to support frames for prosthetic implantable valves. The support frames may include a plurality of symmetrically arrayed interconnected U-shaped member structures. Preferred support frames are tubular structures enclosing a longitudinal axis and including a plurality of U-shaped member structures facing a distal or a proximal end of the support frame. Each U-shaped member structure may be connected to a single longitudinally adjacent U-shaped member facing in an opposite longitudinal direction, as well as two laterally adjacent U-shaped members.

20 Claims, 7 Drawing Sheets

(56) References Cited

U.S. PATENT DOCUMENTS

| | | | |
|---|---|---|---|
| 7,569,071 B2 * | 8/2009 | Haverkost | A61F 2/2418 623/1.24 |
| 7,618,447 B2 * | 11/2009 | Case | A61F 2/2418 623/1.24 |
| 7,806,921 B2 * | 10/2010 | Hoffman | A61F 2/2418 623/1.11 |
| 7,815,677 B2 * | 10/2010 | Jaffe | A61F 2/2409 623/2.14 |
| 7,871,436 B2 * | 1/2011 | Ryan | A61F 2/2418 623/1.15 |
| 7,947,075 B2 * | 5/2011 | Goetz | A61F 2/2418 623/1.15 |
| 8,313,526 B2 * | 11/2012 | Hoffman | A61F 2/2418 623/1.24 |
| 8,398,704 B2 * | 3/2013 | Straubinger | A61F 2/2418 623/1.15 |
| 2003/0149478 A1 * | 8/2003 | Figulla | A61F 2/2418 623/2.38 |
| 2003/0209835 A1 | 11/2003 | Chun et al. | |
| 2004/0019374 A1 | 1/2004 | Hojeibane et al. | |
| 2004/0260389 A1 | 12/2004 | Case et al. | |
| 2005/0075728 A1 | 4/2005 | Nguyen et al. | |
| 2006/0178740 A1 * | 8/2006 | Stacchino et al. | 623/2.18 |
| 2006/0212111 A1 * | 9/2006 | Case | A61F 2/2418 623/1.24 |
| 2006/0276882 A1 * | 12/2006 | Case | A61F 2/07 623/1.24 |
| 2006/0282157 A1 * | 12/2006 | Hill | A61F 2/2418 623/1.24 |
| 2007/0021826 A1 * | 1/2007 | Case | A61F 2/2418 623/1.15 |
| 2007/0027535 A1 * | 2/2007 | Purdy, Jr. | A61F 2/2412 623/2.18 |
| 2007/0038291 A1 | 2/2007 | Case et al. | |
| 2007/0100435 A1 | 5/2007 | Case et al. | |
| 2007/0213813 A1 | 9/2007 | Segesser et al. | |
| 2007/0233237 A1 | 10/2007 | Krivoruchko | |
| 2007/0260327 A1 | 11/2007 | Case et al. | |
| 2007/0282436 A1 * | 12/2007 | Pinchuk | A61F 2/2418 623/2.11 |
| 2007/0288087 A1 * | 12/2007 | Fearnot | A61F 2/2418 623/1.24 |
| 2008/0133005 A1 * | 6/2008 | Andrieu | A61F 2/2418 623/2.13 |
| 2009/0005863 A1 | 1/2009 | Goetz et al. | |
| 2010/0185277 A1 | 7/2010 | Braido et al. | |
| 2010/0262231 A1 * | 10/2010 | Tuval | A61F 2/2418 623/2.4 |
| 2012/0078347 A1 * | 3/2012 | Braido | A61F 2/2418 623/1.26 |
| 2012/0136429 A1 * | 5/2012 | Hinchliffe | A61F 2/2418 623/1.18 |
| 2013/0197622 A1 * | 8/2013 | Mitra | A61F 2/07 623/1.15 |
| 2014/0228937 A1 * | 8/2014 | Krieger | A61F 2/2418 623/1.16 |
| 2015/0018944 A1 * | 1/2015 | O'Connell | A61F 2/2427 623/2.42 |

OTHER PUBLICATIONS

PCT Written Opinion for PCT Application No. PCT/2008/083870, Feb. 18, 2009.

* cited by examiner

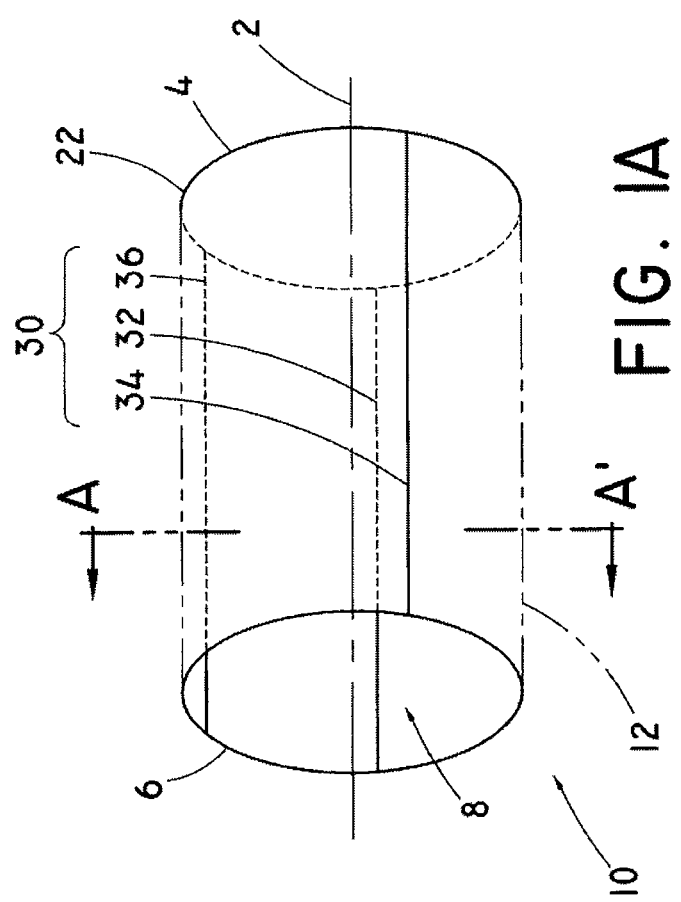

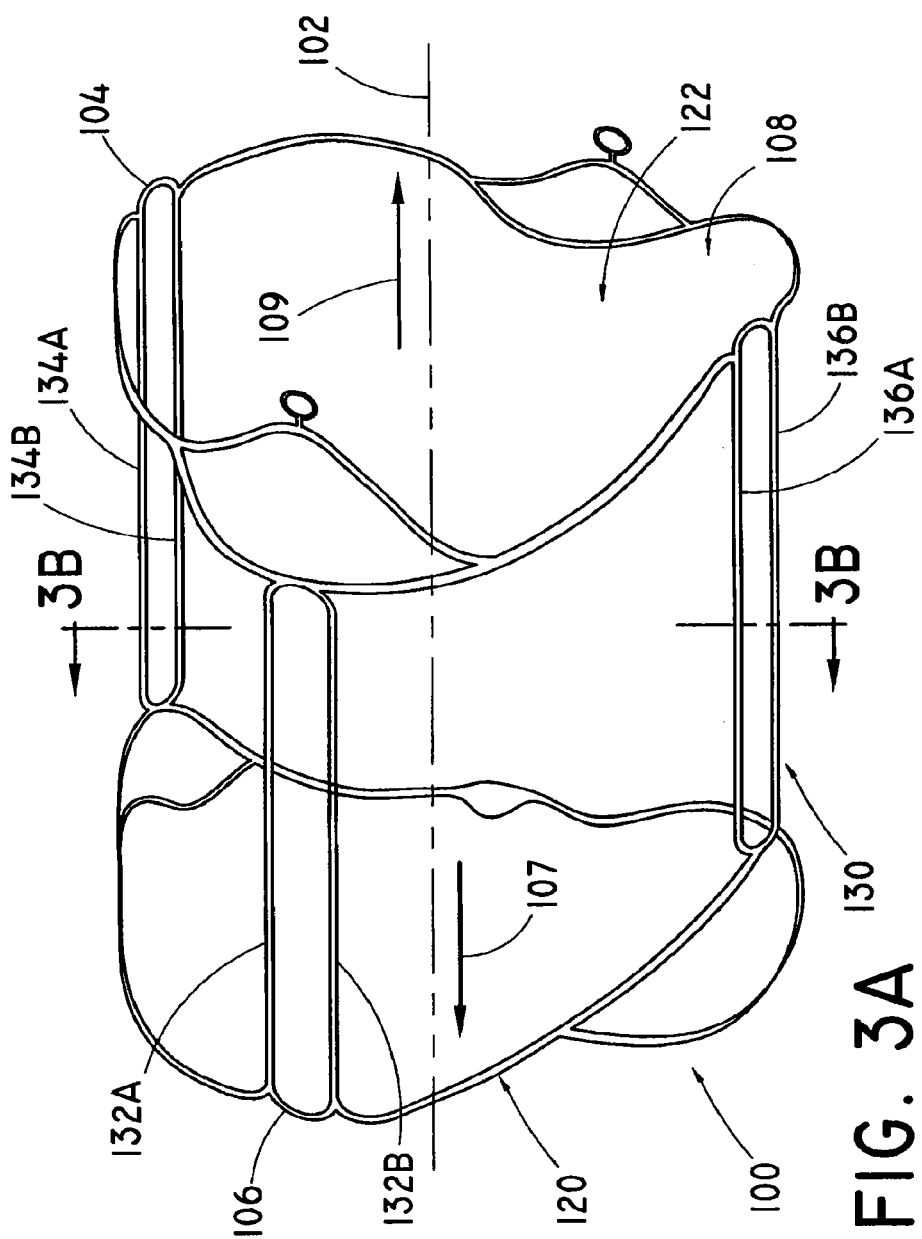

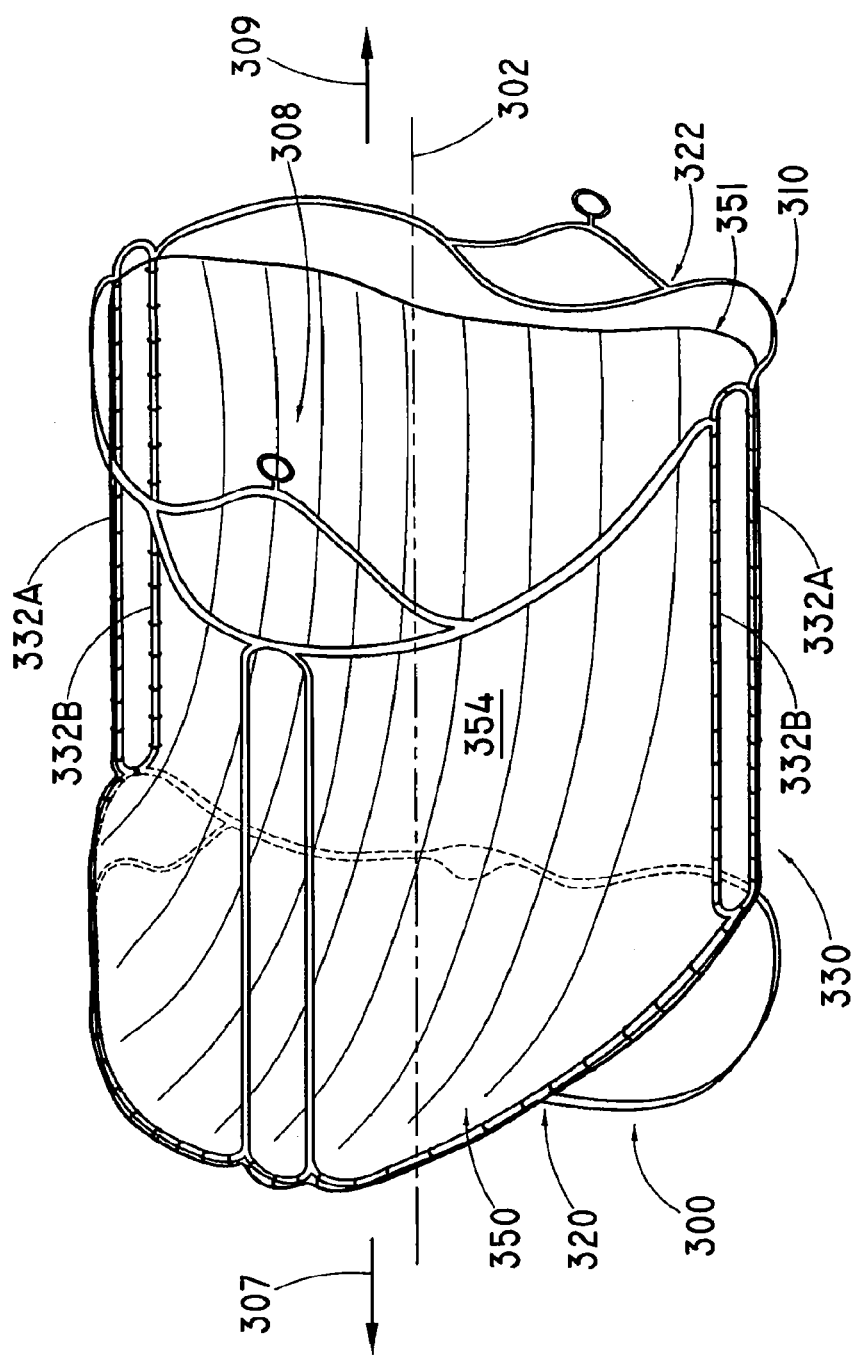

// VALVE FRAME

PRIORITY CLAIM

This application is a continuation of U.S. patent application Ser. No. 12/273,168, which was filed on Nov. 18, 2008 and claims the benefit of U.S. Provisional Patent Application No. 60/988,987, filed Nov. 19, 2007. The entire contents of each of these related applications are hereby incorporated by reference into this disclosure.

TECHNICAL FIELD

The present disclosure relates to support frames for prosthetic implantable valves adapted for percutaneous implantation within a body vessel, as well as methods of treatment pertaining to the implantation of the prosthetic valves and methods of manufacturing prosthetic valves

BACKGROUND OF THE DISCLOSURE

Intraluminally implantable frames may be implanted to treat a variety of conditions in a variety of fields. Frames implanted in vessels, ducts or channels of the human body can form part of a valve to regulate fluid flow within a body lumen or as scaffolding to maintain the patency of the vessel, duct or channel lumen. Implantable frames can also support a valve or valve leaflets for regulating fluid flow within a body lumen or for dilating a body lumen. One or more flexible valve leaflets can be attached to an implantable frame to form a medical device useful as an artificial valve. A variety of other implantable prostheses, such as stents, grafts and the like, also comprise an implantable frame placed within the body to improve the function of a body lumen.

The venous system includes a series of valves that function to assist the flow of blood returning to the heart. These natural valves are particularly important in the lower extremities to prevent blood from pooling in the lower legs and feet during situations, such as standing or sitting, when the weight of the column of blood in the vein can act to prevent positive blood flow toward the heart. This condition, commonly known as chronic venous insufficiency, is primarily found in individuals in which gradual dilation of the veins, thrombotic events, or other conditions prevent the leaflets of the native valves from closing properly. The failure of native valves to properly close can worsen, leading to significant leakage of retrograde flow such that the valve can become incompetent. Chronic venous insufficiency is a condition in which the symptoms can progress from painful edema to skin ulcerations. Elevation of the feet and compression stocking can relieve symptoms, but do not treat the underlying disease. Untreated, the disease can impact the ability of individuals to perform in the workplace or maintain their normal lifestyle.

One promising approach to treating venous valve insufficiency includes the implantation of self-expanding or radially-expandable artificial valves that can be placed using minimally invasive techniques. Recently, the development of artificial and biological valves has been employed to provide additional regulation of blood flow within blood vessels, such as veins. There are a variety of these valves described in the art, which are generally designed to allow normal flow of blood back to the heart, while preventing retrograde flow. However, dynamic fluctuations in the shape of the vein pose challenges to the design of implantable devices that conform to the interior shape of the vein. The shape of a lumen of a vein can undergo dramatic dynamic change as a result of varying blood flow velocities, pressures, and volumes therethrough. Implantable intraluminal prosthetic valves should be compliant enough to conform to the changing shape of the vein lumen and prevent irritation of the wall of the vein contacting the valve, but rigid enough to maintain vein patency and/or valve function within the vein. Blood flow within a vein is intermittent and bidirectional, subject to constant fluctuation in pressure and volume. These conditions may present challenges to designing an implantable frame suitable for placement inside the vein. An implantable frame lacking sufficient radial strength may collapse and/or fracture under the repeated fluctuations of vein diameter, while an implantable frame with undesirably high levels of radial strength may lack flexibility and may damage the vein by failing to compress in response to normal fluctuations in the vein diameter. Likewise, an implantable frame with a high surface area contacting the interior wall of a vein may induce inflammation or trauma in the vein wall, while an implantable frame with an insufficient surface area may lack sufficient durability.

What is needed is an intraluminally-placed medical device, such as a support frame, that provides structure for an artificial valve and is configured to distribute stress and strain forces within the frame during dynamic movement of a body vessel and intermittent fluid flow within the body vessel. In addition, medical devices are needed that provide sufficient radial strength to maintain vessel patency while being configured to prevent migration within the body vessel and minimize irritation of the body vessel. There also remains a need for a support frame configured with a radial strength to maintain patency of a body vessel while supporting a means for regulating fluid within the body vessel and minimizing irritation to the body vessel after implantation and/or extensive wear to the prosthetic valve leaflets during leaflet motion.

SUMMARY

In a first example, implantable medical devices comprising a support frame are provided. The support frame may have a proximal annular member longitudinally spaced from a distal annular member axially aligned with the proximal annular member around a longitudinal axis, and plurality of longitudinal connecting members extending substantially parallel to the longitudinal axis from the proximal annular member to the distal annular member. The outer surface of the support frame may define a hypothetical circumferential plane and an interior tubular lumen around the longitudinal axis extending from a proximal end to a distal end of the support frame. The support frame may be formed from any biocompatible material, such as a shape memory metal or stainless steel.

The plurality of longitudinal connecting members connecting the proximal and distal annular members is each preferably substantially straight and oriented substantially parallel to each other and the longitudinal axis. The members may have a substantially equal length, and preferably define a portion of the circumferential plane between the distal and proximal annular members. The position of the longitudinal connecting members around the circumferential plane of the frame may be selected to provide support frames with desirable properties, such as improved contact between a portion of a valve leaflet and the wall of a body vessel and/or improved symmetrical distribution of stress-strain forces within the frame. The support frame may be described with respect to one or more circumferential distances measured along the circumferential plane perpendicular to the longitudinal axis at a position between the proximal end and the distal end. The support frame may define a plurality of open cells in the hypothetical circumferential plane including the abluminal surface of the support frame in communication with the lumen defined by the support frame around the longitudinal axis. For example, the support frame may provide a single open cell in the circumferential plane extending laterally between two adjacent longitudinal connecting members opposably positioned across the lumen with respect to each other.

The support frame may have any suitable number of longitudinal connecting members. Preferably, the support frame has three or more members including at least two members opposably positioned with respect to each other across the lumen. For instance, the plurality of longitudinal connecting members may consist of three to six straight members oriented parallel to the longitudinal axis. Most preferably, the support frame includes one or more paired longitudinal connecting members extending substantially parallel to the longitudinal axis from the proximal annular member to the distal annular member and defining a circumferential plane around the outer surface of the support frame and a tubular lumen around the longitudinal axis and extending from a proximal end to a distal end of the support frame. The plurality of paired longitudinal connecting members may consist of (n) pairs of closely spaced member pairs including a first member pair opposably positioned across the lumen from a circumferentially adjacent second closely spaced member pair, and (n−2) pairs of closely spaced members circumferentially positioned between the first member pair and the second member pair, where (n) is an integer of 3 or more.

In a second example, the medical device is a medical device including a support frame according to the first example, in combination with a means for regulating fluid flow in a body vessel. The prosthetic valve is preferably an intraluminally-implantable valve prosthesis comprising a support frame attached to at least one valve leaflet. The prosthetic valve may be a venous valve having a flexible leaflet with a vessel-engaging portion. One or more leaflets attached to the support frame may be formed from an extracellular matrix material or a portion of an explanted tissue valve. The implantable prosthetic valve preferably includes one or more valve leaflets attached to the support frame and moveable within the lumen to regulate fluid flow therein. The valve leaflet may be attached to the first member and is moveable across the lumen between an open position, permitting fluid flow through the lumen from the proximal end to the distal end, and a closed position substantially preventing fluid flow through the lumen, the valve leaflet preferably contacting the hypothetical circumferential plane opposite the third member in the closed position.

Delivery systems including a prosthetic valve device and device for deploying the prosthetic valve, such as a catheter, are also provided. Suitable percutaneous deployment devices may include a balloon catheter having adaptations for selectively forcing a portion of the prosthetic valve against the vessel wall, and/or adaptations for radially expanding and compressing the support frame. The prosthetic valve device may be releasably attached to the deployment device by any suitable means including by the use of adhesives or removable elements such as removable sutures.

In a third example, methods for treating venous insufficiency are provided, wherein the method includes deploying a support frame and/or a prosthetic venous valve such as that described above so as to force the valve body against the vascular wall, and selectively attach edges of the valve body against the vascular wall, to seat the valve within the vein. In another aspect of the third example, methods for modifying blood flow in a vascular vessel are also provided.

Other systems, methods, features and advantages will be, or will become, apparent to one with skill in the art upon examination of the following figures and detailed description. It is intended that all such additional systems, methods, features and advantages be included within this description, be within the scope of the disclosure, and be protected by the following claims.

BRIEF DESCRIPTION OF THE DRAWINGS

The medical device may be better understood with reference to the following drawings and description. The components in the figures are not necessarily to scale, emphasis instead being placed upon illustrating the principles of the disclosure. Moreover, in the figures, like referenced numerals designate corresponding parts throughout the different views.

FIG. 1A is a side view of one example of a first support frame.

FIG. 3A is a perspective view of a fifth support frame.
FIG. 4 is a perspective view of a prosthetic valve comprising the fifth support frame.

DETAILED DESCRIPTION

Figure 1B:
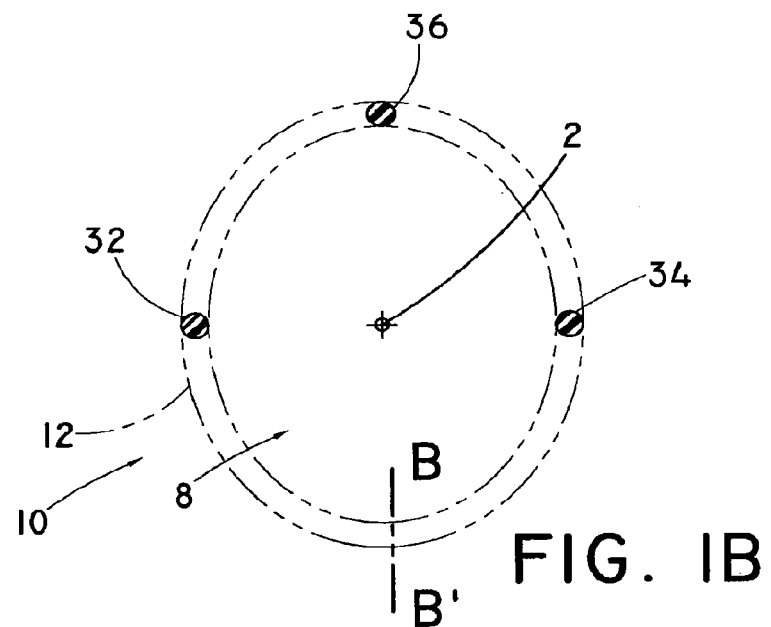
FIG. 1B is a cross sectional view of a portion of the first support frame.

Unless otherwise defined, all technical and scientific terms used herein have the same meaning as commonly understood by one of ordinary skill in the art to which this disclosure pertains. In case of conflict, the present document, including definitions, will control. Preferred methods and materials are described below, although methods and materials similar or equivalent to those described herein can be used in the practice or testing of the present disclosure. All publications, patent applications, patents and other references mentioned herein are incorporated by reference in their entirety. The materials, methods, and examples disclosed herein are illustrative only and not intended to be limiting.

Definitions

The terms "proximal" and "distal" will be used to describe the opposing axial ends of the medical device, as well as the axial ends of various component features. The term "proximal" is used in its conventional sense to refer to the end of the device (or component thereof) that is closest to the operator during use of the device. The term "distal" is used in its conventional sense to refer to the end of the device (or component thereof) that is initially inserted into the patient, or that is closest to the patient.

The term "circumferential" or "circumferentially" refers to a direction or displacement measured along the exterior surface area of an assembled implantable frame in the expanded configuration that is transverse to the longitudinal axis of the implantable frame. The recitation of a first structural feature "circumferentially adjacent" to a second structural feature means that the first structural feature is the nearest first structural feature to the second structural feature when moving circumferentially along the exterior surface of an implantable frame. The term "circumferential distance" means distance measured along the exterior surface of an implantable frame in the expanded configuration.

Unless otherwise indicated, the term "longitudinal" or "longitudinally" refers to a direction measured along the longitudinal axis of the medical device, or a portion thereof such as an implantable frame. The term "longitudinally opposite" means positioned in a distal or proximal direction along the exterior surface of a medical device, such as an implantable frame, parallel to the longitudinal axis of the implantable frame. For example, the recitation of a first structural feature "longitudinally adjacent" to a second structural feature of an implantable frame means that the first structural feature is the nearest first structural feature to the second structural feature when moving longitudinally along the exterior surface of the implantable frame. Unless otherwise indicated, the term "longitudinal distance" measured between two structural features of an implantable frame means a distance or displacement measured parallel to the longitudinal axis of the implantable frame in the expanded configuration, measured along the exterior surface area of the implantable frame.

Terms such as "preferably," "desirably," "commonly," and "typically" are not utilized herein to limit the scope of the claimed disclosure or to imply that certain features are critical, essential, or even important to the structure or function of the claimed disclosure. Rather, these terms are merely intended to highlight alternative or additional features that may or may not be utilized in a particular example of the present disclosure.

Prosthetic Valves with Preferred Support Frame Configurations

In a first example, implantable medical devices including a support frame having a preferred geometry are provided. In particular, the support frame preferably includes multiple longitudinal connecting members circumferentially arranged in particularly preferred positions relative to one another. The preferred support frame geometries can be illustrated with respect to the following examples, which serve to illustrate certain preferred aspects of the first example of the disclosure.

FIG. 1A shows a side view of a first preferred support frame geometry. The support frame 10 may have a proximal annular member 22 longitudinally spaced from a distal annular member 20 at the distal end 6 of the support frame 10 and axially aligned with the proximal annular member 22 around a longitudinal axis 2 at the proximal end 4 of the support frame 10, as well as a plurality of longitudinal connecting members 30 (including 32, 34, 36) extending substantially parallel to the longitudinal axis 2 from the proximal annular member 22 to the distal annular member 20. The support frame 10 may define a hypothetical circumferential surface plane 12 around the outer surface of the support frame 10 and a tubular lumen 8 around the longitudinal axis and extending from a proximal end to a distal end of the support frame. The support frame 10 may be formed from any biocompatible material, such as a shape memory metal or stainless steel.

The support frame may have any suitable number of longitudinal connecting members 30. Preferably, the support frame has three or more members including at least two members opposably positioned with respect to each other across the lumen 8. For instance, the plurality of longitudinal connecting members 30 may consist of three to six longitudinal connecting members oriented parallel to the longitudinal axis 2. The plurality of longitudinal connecting members 30 ("members") are each preferably substantially straight and oriented substantially parallel to each other and the longitudinal axis 2.

Figure 1C:
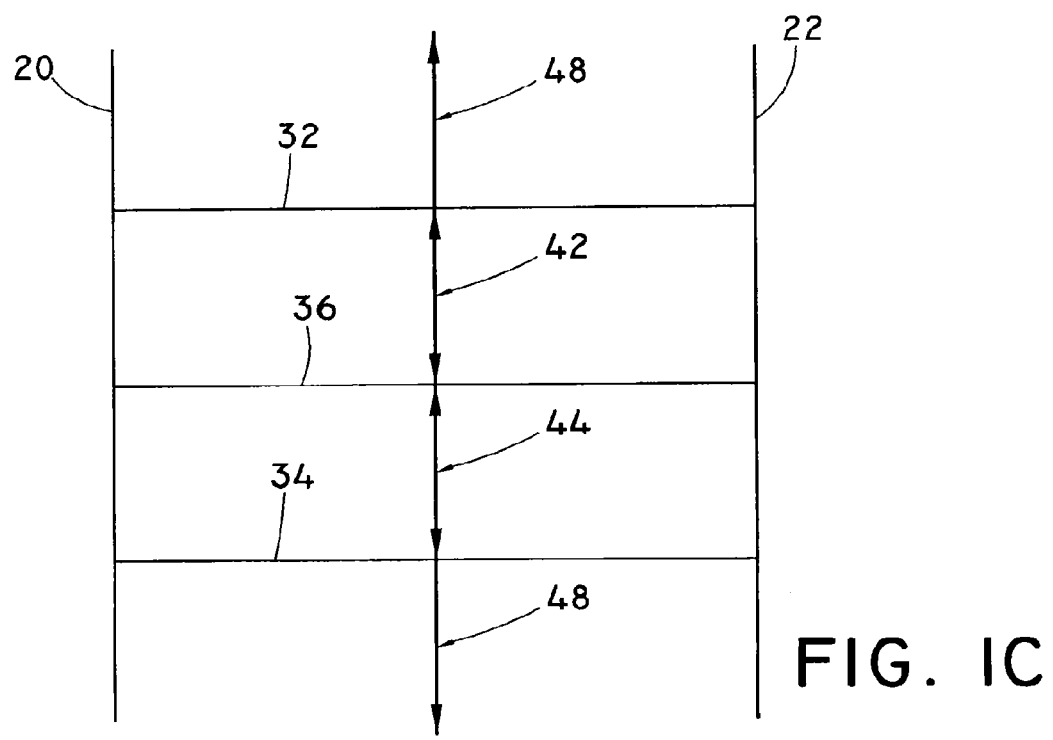
FIG. 1C is a flat plan view of the first support frame shown in FIGS. 1A and 1B.

In one example, a support frame may have three members oriented substantially parallel to one another, with a first circumferential distance between the first member and the third member being substantially equal to a second circumferential distance between the third member and the second member, and the first member and second member being opposably positioned and circumferentially adjacent with respect to each other (e.g., at a radial angle of about 2.pi./2 radians with respect to one another). FIGS. 1A-1C show a first example of a support frame 10. The first support frame 10 has three longitudinal connecting members 30: a first member 32, a second member 34 and a third member 36. The members 30 may have a substantially equal lengths, may each be positioned at a substantially equal radial distance from the longitudinal axis 2 and preferably each define a portion of the hypothetical circumferential surface plane 12 between the distal annular member 20 and proximal annular member 22. The position of the longitudinal connecting members 30 around the circumferential plane of the frame may be selected to provide support frames 10 with desirable properties, such as improved contact between a portion of a valve leaflet and the wall of a body vessel and/or improved symmetrical distribution of stress-strain forces within the frame. The support frame 10 may be described with respect to one or more circumferential distances measured along the circumferential plane perpendicular to the longitudinal axis at a position between the proximal end and the distal end.

FIG. 1B is a cross-section of the support frame 10 along line A-A' shown in FIG. 1A, showing the relative positions of the three members 30. The first member 32 is circumferentially adjacent to the second member 34 and the third member 36; the second member 34 is circumferentially adjacent to the first member 32 and the third member 36; and the third member 36 is circumferentially adjacent to the first member 32 and the second member 34. The first member 32 and the second member 34 are opposably positioned across the lumen 8 defined by the support frame 10. The third member 36 may be positioned at a substantially equal circumferential distance from the first member 32 and the second member 34. A radial angle of about 2.pi./4 is preferably subtended between both the first member 32 and the third member 36 and between the second member 34 and the third member 36. A radial angle of about 2.pi./2 is preferably subtended between the opposably positioned first member 32 and second member 34.

Cylindrical support frames, as shown in FIG. 1A, may be obtained from the pattern shown in a flat plan view by cutting the pattern of the flat plan view from a cylindrical tube of the support frame material or from a flat piece of the support frame material, which is then rolled and joined to form the support frame by any suitable method. Methods of cutting the flat plan pattern into the support frame material include laser cutting and chemical etching. Preferably, the support frames are cut from a tube or cannula of shape memory metal to provide a radially self-expanding support frame. When forming the support frame from shape memory metal such as nitinol, the support frame can be laser cut from a nitinol tube. Thereafter, the support frame can be subjected to a shape-setting process in which the cut tube is expanded on a mandrel and then heated. Multiple expansion and heating cycles can be used to shape-set the support frame to the final expanded diameter. Preferably, the final expanded diameter is equal to the desired deployed diameter of the support frame. During expansion, the support frame is preferably axially restrained such that the length of the support frame does not change during expansion. The finished support frame preferably has an austenite finish temperature less than body temperature. Thus, at body temperature, the support frame will self-expand to the desired deployed diameter due to the shape memory characteristic of the metal forming the support frame.

FIG. 1C shows a flat plan view of the support frame 10 formed by hypothetically "cutting" the support frame 10 along line B-B' shown in FIG. 1B and "unrolling" the support frame 10 to flatten the hypothetical circumferential surface plane 12 described above. The flat plan view shows the three longitudinal connecting members 30 extending between the proximal annular member 22 and the distal annular member 20, including the first member 32 and the third member 36 spaced apart by a first distance 42 and the second member 34 and the third member 36 spaced apart by a second distance 44 and the second member 34 spaced from the first member 32 by a third distance 48. In the tubular configuration shown in FIG. 1A, the first distance 42, the second distance 44 and the third distance 46 are circumferential distances measured along the hypothetical circumferential surface plane 12 containing the outer (abluminal) surface of the support frame 10, the circumferential distances being measured perpendicular to the longitudinal axis 2 at a fixed longitudinal point between the distal end 6 and proximal end 4 of the support frame 10.

As shown in FIG. 1A and FIG. 1C, the support frame 10 may define a plurality of open cells in the hypothetical circumferential plane including the abluminal surface of the support frame in communication with the lumen defined by the support frame around the longitudinal axis. For example, the support frame may provide a first single open cell in the circumferential plane extending laterally between first (32) and second (34) longitudinal connecting members, which are opposably positioned across the lumen 8 with respect to each other. Two other smaller open cells of substantially congruent geometries may be defined by the support frame 10 between the proximal annular member 22 and the distal annular member 20: a second cell between the first (32) and third (36) members and a third cell between the second (34) and third (36) members (respectively).

Figure 2A:
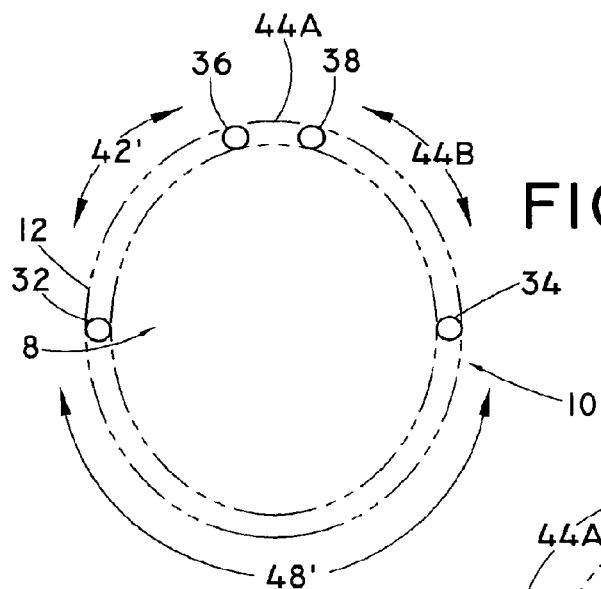
FIG. 2A is a cross sectional view of a second support frame.

In another example, a support frame may have four members oriented substantially parallel to one another. For example, FIG. 2A is a cross-sectional view of a second support frame substantially identical to the support frame 10 in FIGS. 1A-1C, except as described below. The second support frame includes the first member 32, the second member 34, the third member 36 and a fourth member 38 circumferentially adjacent to the third member 36 and the second member 34. In this example, the support frame may have a first circumferential distance 42' between the first member 32 and the third member 36 substantially equal to a second circumferential distance 44b between the fourth member 38 and the second member 34; and a third circumferential distance 44a between the third member 36 and the fourth member 38 is less than about 10% of the longitudinal length of each of the members 30. The support frame in this example is also characterized by a fourth circumferential distance 48' between the first member 32 and the second member 34 that is substantially equal to the sum of the first circumferential distance 42', the second circumferential distance 44b and the third circumferential distance 44a. In this example, the third member 36 and the fourth member 38 are a closely spaced pair of members 30. Support frames where the plurality of longitudinal connecting members 30 includes one or more closely spaced pairs of members are particularly preferred. It is believed that closely paired support members desirably distribute stress-strain forces, particularly in radially expandable support frames. Additionally, closely paired support members may provide for redundancy in attaching a valve thereto, such as providing a second suturing location for securing a valve to the support frame.

Figure 2B:
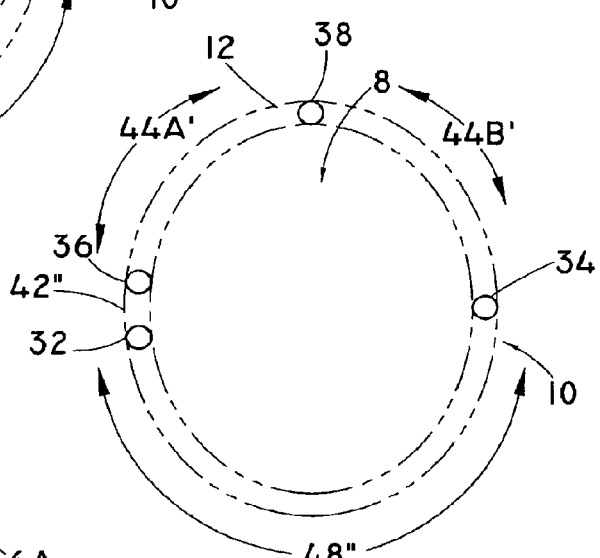
FIG. 2B is a cross sectional view of a third support frame.

Alternatively, the four parallel longitudinal support members in the second support frame may be positioned differently, as shown in the cross sectional view of FIG. 2B. The cross section of a third support frame shown in FIG. 2B is substantially identical to the support frame of FIG. 2A except in the relative circumferential positions of the members 30. In particular, the third support frame cross section in FIG. 2B has a first circumferential distance 42" between the closely paired first member 32 and the third member 36. A first circumferential distance 42" between the first member 32 and the third member 36 is preferably less than about 10% of the longitudinal length of the members 30. A second circumferential distance 44b' is measured between the second member 34 and the fourth member 38. A third circumferential distance 44a' is measured between the third member 36 and the fourth member 38. A fourth circumferential distance 48" is measured between the first member 32 and the second member 34. The second circumferential distance 44b' may be substantially equal to the third circumferential distance 44a' and one-half of the first circumferential distance 42". The first member 32 is positioned opposite the lumen 8 from the second member 34. The radial angle subtended between the fourth member 38 and the second member 34 is preferably about 2.pi./4. The radial angle subtended between the fourth member 38 and the third member 36 is preferably less than 2.pi./4. Preferably, a radial angle of 2.pi./4 is subtended by the sum of (1) the radial angle between the fourth member 38 and the third member 36 and (2) one-half of the angle subtended between the first member 32 and the third member 36. The sum of the radial angle between the first member 32 and the second member 34 and one-half of the radial angle subtended between the first member 32 and the third member 36 is preferably about 2.pi./2.

Figure 2C:
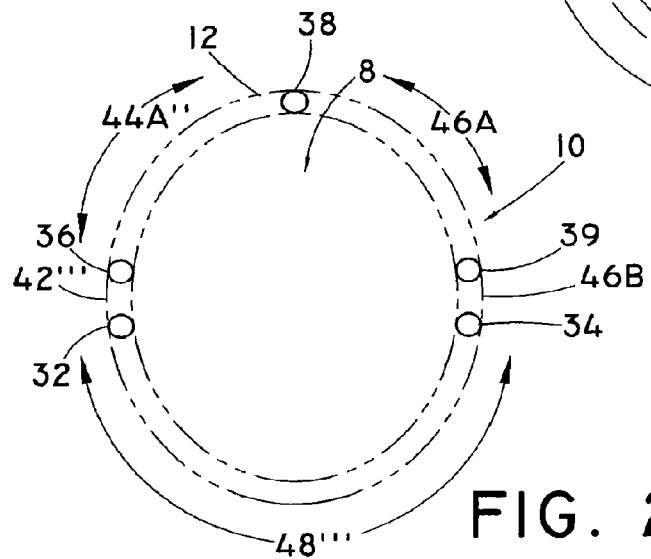
FIG. 2C is a cross sectional view of a fourth support frame.

In another example, the support frame may have five substantially parallel members oriented in the manner shown in FIG. 2C. FIG. 2C is a cross-sectional view of a fourth support frame substantially identical to the first support frame 10 in FIGS. 1A-1C, except with respect to the number and position of the longitudinal connecting members 30 as described below. The plurality of longitudinal connecting members 30 in the fourth support frame consists of five members oriented substantially parallel to one another, including the first member 32, the second member 34, the third member 36, a fourth member 38 circumferentially adjacent to the third member 36 and a fifth member 39 circumferentially adjacent to the second member 34 and the fourth member 38. A first circumferential distance 42∝" extending between the first member 32 and the third member 36 is preferably less than about 10% of the longitudinal length of the members. Similarly, a second circumferential distance 46b measured between the second member 34 and the fifth member 39 is preferably less than about 10% of the longitudinal length of the members. A third circumferential distance 44a" is measured between the circumferentially adjacent third member 36 and the fourth member 38. A fourth circumferential distance 48" is measured between the circumferentially adjacent fourth member 38 and fifth member 39. The first circumferential distance 42'" and the second circumferential distance 46b are preferably substantially equal. The third circumferential distance 44a" is preferably substantially equal to a fourth circumferential distance 46a between the fourth member 38 and the fifth member 39. The support frame may also include a fifth circumferential distance 48'" between the first member 32 and the second member 34 that is substantially equal to the sum of the third circumferential distance 44a" and the fourth circumferential distance 46a. A radial angle of about 2.pi./4 radians is subtended by sum of the third circumferential distance 44a" and one half of the first circumferential distance 42'". Similarly, a radial angle of about 2.pi./4 radians is subtended by sum of the fourth circumferential distance 46a and one half of the second circumferential distance 46b. A radial angle of about 2.pi./2 radians is subtended by sum of the fifth circumferential distance 48", one half of the first circumferential distance 42''' and one half of the second circumferential distance 46b.

Figure 3B:
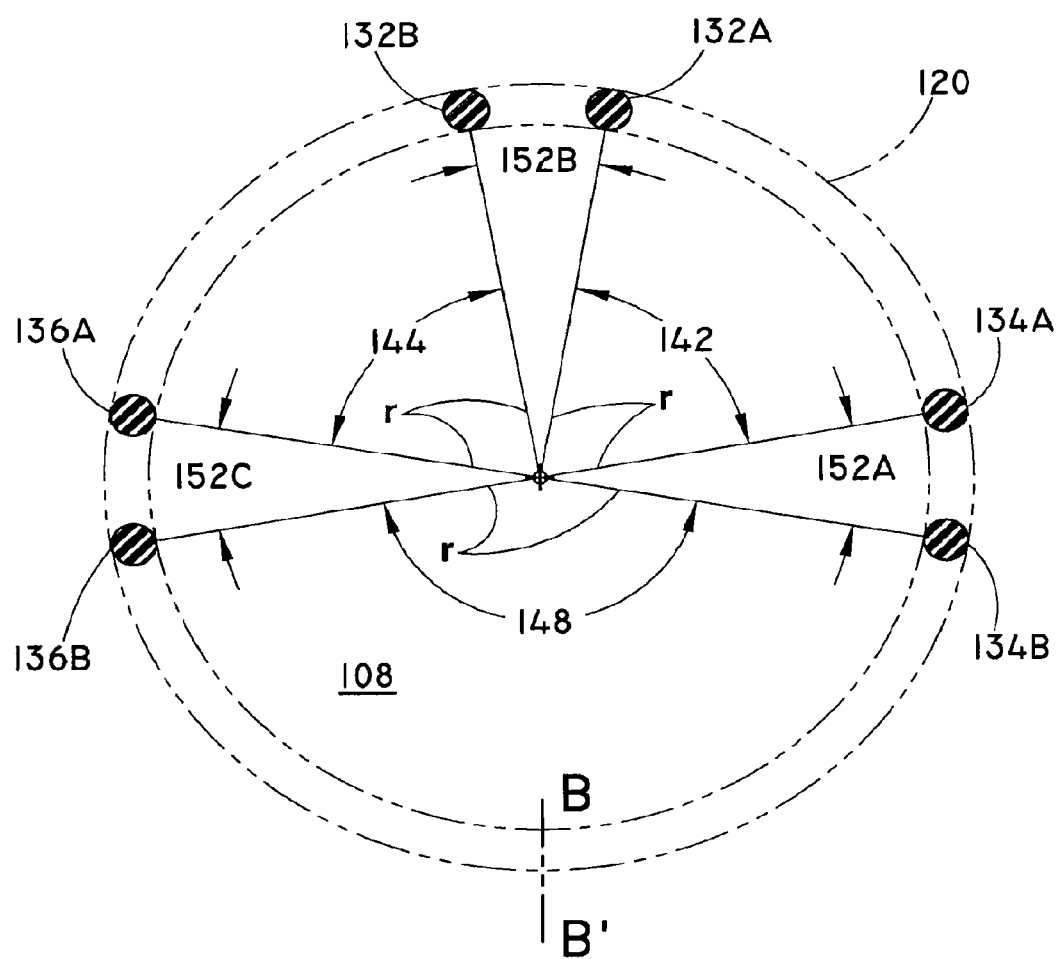
FIG. 3B is a cross sectional view of the fifth support frame.

In another aspect, the support frame has six longitudinal connecting members. FIG. 3A shows a perspective view of a fifth support frame 100 having a plurality of six longitudinal connecting members 130 extending between a proximal annular member 122 and a distal annular member 120. The fifth support frame 100 differs from the support frames discussed above in at least two respects: first, the proximal and distal annular members (120, 122) are sinusoidal hoop members instead of planar ring members and, second, the plurality of longitudinal connecting members 130 has six members. In particular, referring to FIG. 3B, the plurality of longitudinal connecting members may consist of six members 130 oriented substantially parallel to one another, including a first member 136b, a second member 134b, a third member 136a, a fourth member 132b circumferentially adjacent to the third member 136a and a fifth member 132a, the fifth member 132a circumferentially adjacent to the fourth member 132b and a sixth member 134a, the sixth member 134a circumferentially adjacent to the fifth member 132a and the second member 134b. A first circumferential distance 152c may extend between the first member 136b and the third member 136a and be less than about 10% of the longitudinal length of the longitudinal connecting members 130. A second circumferential distance 152a may be measured between the second member 134b and the sixth member 134a and be less than about 10% of the longitudinal length of the members 130. A third circumferential distance 152b may extend between the fourth member 132b and the fifth member 132a and be less than about 10% of the longitudinal length of the members 130. A fourth circumferential distance 144 may be measured between the third member 136a and the fourth member 132b and is preferably substantially equal to a fifth circumferential distance 142 between the fifth member 132a and the sixth member 134a. A sixth circumferential distance 148 is measured between the second member 134b and the first member 136b. Preferably, the sixth circumferential distance 148 is substantially equal to the sum of the fourth circumferential distance 144, the third circumferential distance 152b and the fifth circumferential distance 142. The fourth circumferential distance 144 is preferably substantially equal to the fifth circumferential distance 142.

In one example, the frame may be configured such that when the frame is deployed within a body vessel, an artificial partial sinus is formed adjacent a valve member such that bodily fluids, for example blood, collecting within the pocket formed around the base of the valve member are more likely to be flushed out on a continual basis due to the advantageous geometry created by the valve member and artificial partial sinus.

For example, an artificial partial sinus may be formed by at least one of the longitudinal connecting members. Referring again to FIG. 3A, the fifth member 132a and the fourth member 132b may create an artificial partial sinus. The artificial partial sinus is preferably characterized by a greater lateral distance between a portion of the longitudinal connecting members (132a, 132b) and the longitudinal axis 102 than between proximal and distal annular members (120, 122) and the longitudinal axis 102. The partial sinus is preferably formed by the longitudinal connecting members (132a, 132b) curving or arching away from the lumen 108.

The configuration of the partial sinus may depend on several factors, including body vessel diameter, valve member geometry such as length, slack, and orientation, fluid column pressures at the site of deployment, and other factors. For example, the partial sinus may have a longitudinal length at least as great as the longitudinal length of the valve member, permitting the valve member to fully retract within the partial sinus, thereby substantially uninterrupting antegrade flow.

The support frames preferably include one or more paired longitudinal connecting members extending substantially parallel to the longitudinal axis from the proximal annular member to the distal annular member and defining a circumferential plane around the outer surface of the support frame and a tubular lumen around the longitudinal axis and extending from a proximal end to a distal end of the support frame. The plurality of paired longitudinal connecting members may consist of (n) pairs of closely spaced member pairs including a first closely-spaced member pair opposably positioned across the lumen from a circumferentially adjacent second closely spaced member pair, and (n−2) pairs of closely spaced members circumferentially positioned between the first closely-spaced member pair and the second member pair, where (n) is an integer of 3 or more. Preferably, (n) is an integer of 3 or more, including integers of 3, 4, 5, 6, 7, 8, 9, 10 or more.

As used herein, "closely-spaced pairs" of longitudinal connecting members are circumferentially adjacent longitudinal connecting members that are circumferentially separated by a distance that is less than about 15% of their length, and preferably less than 10%. Pairs of closely-spaced longitudinal connecting members are preferably positioned at substantially equal circumferential distances from circumferentially adjacent pairs of longitudinal connecting members. The circumferential distance between each pair of closely spaced members is preferably less than about 10% of the longitudinal length of the members. For example when (n) is 3, the support frame may include a third closely spaced member pair positioned symmetrically between the first member pair and the second member pair, the support frame having a first circumferential distance between the first member pair and the third member pair that is substantially equal to a second circumferential distance between the third member pair and the second member pair.

FIG. 3B is a cross sectional view of the fifth support frame 100 between the proximal annular member 122 and the distal annular member 120. The sixth support frame 100 includes three closely spaced pairs of longitudinal connecting members. The plurality of paired longitudinal connecting members 130 extend substantially parallel to the longitudinal axis from the proximal annular member 122 to the distal annular member 120 and define a hypothetical circumferential plane around the outer surface of the support frame 100 and a tubular lumen 108 around the longitudinal axis 102 and extending from a proximal end 104 to a distal end 106 of the support frame 100. The first circumferential distance 152c, the second circumferential distance 152a and the third circumferential distance 152b are all preferably substantially equal, and are each preferably less than about 10% of the longitudinal length of any of the members 130. The close spacing of the first and third members (136a, 136b), the fourth and fifth members (132a, 132b) and/or the second and sixth members (134a, 134b) desirably distributes stress and strain sustained at the connections between the longitudinal connecting members 130 to the proximal annular member 122 and the distal annular member 120, particular during radial compression of the support frame 100. Additionally, close spacing of the members, for example the first and third members (136a, 136b), the fourth and fifth members (132a, 132b) and/or the second and sixth members (134a, 134b), may provide for redundancy in attaching a valve thereto, such as providing a second suturing location for securing a valve to the support frame.

Alternative examples provide support frames with two, three, four, five, six or more pairs of longitudinal connecting members. Preferably, at least two pairs of circumferentially adjacent longitudinal connecting members are positioned across the lumen 108 from each other.

Figure 3C:
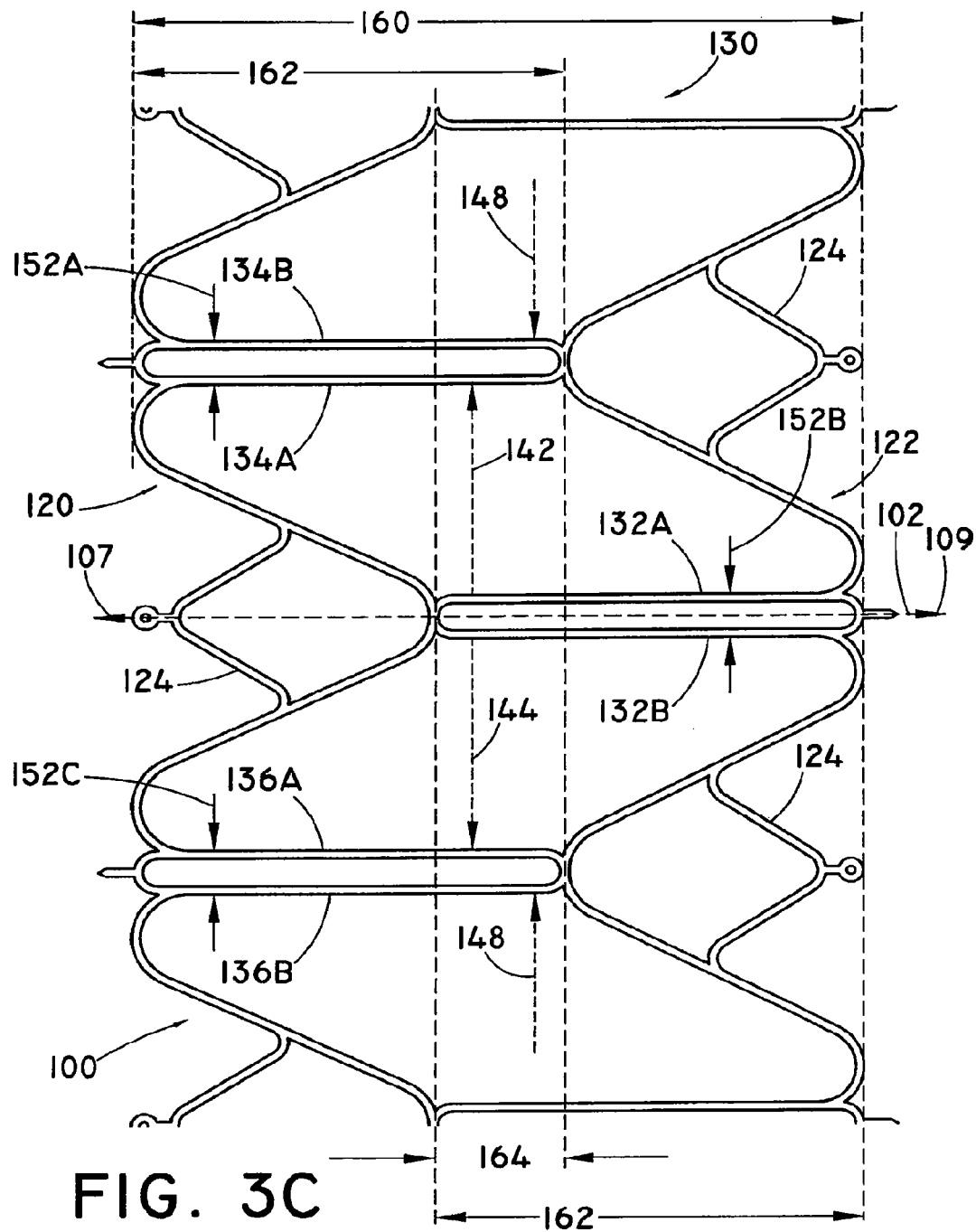
FIG. 3C is a flat plan view of the fifth support frame.

FIG. 3C is a flat plan view of the fifth support frame 100, formed by theoretically "cutting" the cross section of FIG. 3B along line B-B' and "unrolling" the support frame 100 into a flat plane corresponding to the hypothetical circumferential plane forming the outer surface of the support frame 100 in the tubular configuration shown in FIG. 3A. Alternatively, the tubular support frame 100 may be formed by laser cutting a cylindrical cannula of biocompatible metal according to the pattern shown in FIG. 3C. The support frame 100 has a total longitudinal length 160. The proximal annular member 122 and distal annular member 120 are spaced apart by a first longitudinal distance 164. The plurality of six longitudinal connecting members 130 each has a substantially equal length 162. The support frame 100 also includes three reinforcing members 124. The reinforcing members 124 are joined at both ends to a single annular member, such as the distal annular member 120 or the proximal annular member 122, and can have the same or different shapes.

Implantable Support Frame Compositions

The support frame may be formed from any suitable material. Preferred materials for frames include those materials that can provide the desired functional characteristics with respect to mechanical load bearing, biological compatibility, modulus of elasticity, radio-opacity, or other desired properties. For some examples, the materials used to form the implantable frames can comprise a material that exhibits excellent corrosion resistance. For some examples, the material can be selected to be sufficiently radiopaque and create minimal artifacts during magnetic resonance imaging techniques (MRI). In some examples, the implantable frame can comprise a metal, a metal alloy, a polymer, or any suitable combination thereof, for example as frame with multiple layers.

Preferably, the support frames are self-expanding comprising a material capable of significant recoverable strain to assume a low profile for delivery to a desired location within a body lumen. After release of the compressed self-expanding stent, it is preferred that the frame be capable of radially expanding back to its original diameter or close to its original diameter. Accordingly, some examples provide frames made from material with a low yield stress (to make the frame deformable at manageable balloon pressures), high elastic modulus (for minimal recoil), and is work hardened through expansion for high strength. Particularly preferred materials for self-expanding implantable frames are shape memory alloys that exhibit superelastic behavior, i.e., are capable of significant distortion without plastic deformation. Frames manufactured of such materials may be significantly compressed without permanent plastic deformation, i.e., they are compressed such that the maximum strain level in the stent is below the recoverable strain limit of the material. Discussions relating to nickel titanium alloys and other alloys that exhibit behaviors suitable for frames can be found in, e.g., U.S. Pat. No. 5,597,378 (Jervis) and WO 95/31945 (Burmeister et al.). A preferred shape memory alloy is Ni—Ti, although any of the other known shape memory alloys may be used as well. Such other alloys include: Au—Cd, Cu—Zn, In—Ti, Cu—Zn—Al, Ti—Nb, Au—Cu—Zn, Cu—Zn—Sn, CuZn—Si, Cu—Al—Ni, Ag—Cd, Cu—Sn, Cu—Zn—Ga, Ni—Al, Fe—Pt, U—Nb, Ti—Pd—Ni, Fe—Mn—Si, and the like. These alloys may also be doped with small amounts of other elements for various property modifications as may be desired and as is known in the art. Nickel titanium alloys suitable for use in manufacturing implantable frames can be obtained from, e.g., Memry Corp., Bethel, Conn. One suitable material possessing desirable characteristics for self-expansion is Nitinol, a Nickel-Titanium alloy that can recover elastic deformations of up to 10 percent. This unusually large elastic range is commonly known as superelasticity.

Alternatively, the implantable frames are designed to be expanded by a balloon or some other device (i.e., the frames are not self-expanding), and may be manufactured from an inert, biocompatible material with high corrosion resistance that can be plastically deformed at low-moderate stress levels, such as tantalum. The implantable frames can be deployed by both assisted (mechanical) expansion, e.g. balloon expansion, and self-expansion means. In examples where the implantable frame is deployed by mechanical (balloon) expansion, the implantable frame is made from materials that can be plastically deformed through the expansion of a mechanical assist device, such as by the inflation of a catheter based balloon. When the balloon is deflated, the frame can remain substantially in the expanded shape. Other acceptable materials include stainless steel, titanium ASTM F63-83 Grade 1, niobium or high carat gold K 19-22. One widely used material for balloon expandable structures is stainless steel, particularly 304 and 316L stainless steel. This material is particularly corrosion resistant with a low carbon content and additions of molybdenum and niobium. Fully annealed, stainless steel is easily deformable. Alternative materials for mechanically expandable structural frames that maintain similar characteristics to stainless steel include tantalum, platinum alloys, niobium alloys, and cobalt alloys.

Optionally, the support frame may be formed from or coated with other materials, such as polymers and bioabsorbable polymers may be included in or on the implantable support frames. The support frames or portions thereof can optionally comprise material that permits identification of the position or orientation of the frame within a body passage. Radiopaque markers are advantageously positioned at one or more ends of the implantable frame to aid the physician in positioning the frame at a site inside a body vessel. For example, portions of the implantable frame can include a radiopaque material that can be identified by X-rays. For example, U.S. Pat. No. 6,409,752, issued Jun. 25, 2002 to Boatman et al., incorporated herein by reference, discloses various radiopaque materials that can be used in or on the implantable frames.

The implantable frames may be fabricated using any suitable method known in the art. Preferably, the complete frame structure is cut from a solid tube or sheet of material, and thus the frame would be considered a monolithic unit. Laser cutting, water-jet cutting and photochemical etching are all methods that can be employed to form the structural frame from sheet and tube stock. Still other methods for fabricating the complete frame structure as previously disclosed would be understood by one of skill in the art.

Alternatively, the frame can also be formed from wire using wire forming techniques, such as coiling, braiding, or knitting. By welding the wire at specific locations a closed-cell structure may be created. This allows for continuous production, i.e. the components of the implantable frame may be cut to length from a long wire mesh tube. In addition, an implantable frame is constructed from sheet, wire (round or flat) or tubing. The method of fabrication can be selected by one skilled in the art depending on the raw material used.

Techniques for forming implantable frames are discussed, for example, in Dougal et al., "Stent Design: Implications for Restenosis," Rev. Cardiovasc Med. 3 (suppl. 5), S16-S22 (2002), which is incorporated herein by reference in its entirety.

In some examples, connections between the U-shaped member of each portion to the U-shaped member of an adjacent portion in mirror symmetry at the first and second connections, as well as the connection between the supporting arms and the U-shaped member and the struts 32 and bends of the supporting arms, may be by welding or other suitable connecting means. Other connection means include the use of a binder, heat, or chemical bond, and/or attachment by mechanical means, such as pressing, welding or suturing. In addition, portions of the frame may be attached by applying a bonding coating.

A support frame can optionally be sterilized using any suitable technique known in the art, or equivalents thereto. For example, an implantable frame can be sterilized using ethylene oxide sterilization, as described in AAM/ISO 11135:1994 "Medical Devices—Validation and Routine Control of Ethylene Oxide Sterilization," incorporated herein by reference in its entirety. In some examples, a sterilized implantable frame satisfies a minimum Sterility Assurance Level (SAL) of about 10.sup.−6.

Prosthetic Valve Devices

In a second example, prosthetic valve devices are provided. The prosthetic valve preferably includes a support frame described with respect to the first example and a means for regulating fluid through a body vessel. Preferably the prosthetic valve prosthesis devices are configured to treat incompetent or damaged cardiac or venous valves in mammals or to otherwise beneficially modify fluid flow in a bodily passage. For example, a prosthetic valve may be configured to replace or augment the function of natural venous valves operative in veins. The prosthetic venous valve preferably includes a support frame of the first example designed to resist collapsing under the contraction of the muscle present around veins by symmetrically distributing stress and strain within the frame.

A second non-limiting example of a suitable prosthetic valve device 300 is shown in FIG. 4, which includes a flexible valve member attached to a first tubular support frame described above with respect to FIGS. 3A-3C. Other prosthetic valves can be formed by attaching a means for regulating fluid flow, such as a valve leaflet or monocuspid valve member, to any support frame described according to the first example. One or more prosthetic valves can be implanted within a tubular body passage of a patient, especially a human, including for example in veins or arteries, to regulate fluid flow therein.

With reference to FIG. 4, a prosthetic valve 300 includes a support frame 310, which may be similar to the frame 100 described above, with six longitudinal connecting members 330 extending between a proximal annular member 322 and a distal annular member 320. Support frame 310 includes a proximal annular member 322 that differs from the proximal annular member 122 in that the member 124 forms part of the annular member 322. A valve member, such as monocuspid valve member 350 is attached to the support frame 310. The monocuspid valve member 350 is configured and attached in a manner to allow a portion of the monocuspid valve member 350 to extend across the lumen 308 of the support frame 310. Preferably, the support frame 310 is radially self-expanding with a maximum diameter that is slightly greater than the body vessel where the prosthetic valve 300 is implanted, such that the support frame 310 exerts sufficient outward radial force against the inner wall of the body vessel to retain the prosthetic valve 300 therein. Alternatively, the support frame 310 may include one or more means to anchor the support frame 310 within a body vessel, such as barbs or adhesives disposed on the outer, vessel-contacting portion of the support frame 320 (not shown).

Support frames where the plurality of longitudinal connecting members includes one or more circumferentially adjacent pairs of members separated by a circumferential distance that is less than the length of the members are particularly preferred. Preferably, two or more circumferentially adjacent longitudinal connecting members are closely spaced member pairs. It is believed that closely paired support members desirably distribute stress-strain forces, particularly in radially expandable support frames.

In a vein, blood flow occurs in an intermittent nature, with surges in antegrade fluid flow occurring between intermittent retrograde fluid flow. A prosthetic venous valve 300 preferably provides a one-way valve that permits intermittent blood flow in an antegrade direction 309 while minimizing the retrograde fluid flow in the opposite direction 307. The monocuspid valve member 350 is a flexible structure configured to moveably traverse the lumen 308 of the support frame 310, and configured to sealably engage the opposite wall of the vein through a portion of the opposite side of the support frame 310. In this example, wear on the valve member may be decreased and may provide for improved sealing against the wall of the vein. The monocuspid valve member 350 may be configured as a single leaflet attached to a first closely-spaced pair of longitudinal connecting members 332a and 332b and a second closely-spaced pair of longitudinal connecting member 334a and 334b, which may be positioned opposite one another across the lumen 308. The monocuspid valve member 350 can be formed from a suitably flexible material that is responsive to fluid flow contacting the surface, and can be sized to extend transversely across the lumen 308 of the support frame 310, in a path substantially perpendicular to the longitudinal axis 302.

The monocuspid valve member 350 can be oriented with the retrograde surface of the leaflet facing the direction of longitudinal retrograde fluid flow through lumen 308. For example, in a vein, the direction of retrograde fluid flow 307 is away from the heart, while antegrade fluid flow direction 309 proceeds along the longitudinal axis 302 in the direction toward the heart. During retrograde fluid flow 307, blood passes the free edge 351 (unattached to the support frame 310) of the monocuspid valve member 350, urging the leading edge to transversely cross the lumen 308 and sealably engage the vein wall as blood fills the monocuspid valve member 350. The monocuspid valve member 350 may have a closed or substantially closed end and an open end (e.g., free edge 351). The monocuspid valve member 350 quickly fills with the retrograde flowing blood, decreasing blood flow through the prosthetic valve 300 in the retrograde direction 307 to assume the closed configuration shown in FIG. 4. In the closed configuration, blood fills the "pocket" 354 of the monocuspid valve member 350, which completely fills the lumen 308 and minimizes fluid flow through the prosthetic valve 300 in the retrograde direction 307.

When blood flow in the antegrade direction 309 occurs, blood exerts pressure on the antegrade surface of the monocuspid valve member 350, urging the free edge 351 back across the lumen 308 and forcing out fluid collected in the pocket 354 portion of the monocuspid valve member 350. As the monocuspid valve member 350 opens, the free edge 351 is forced toward vessel wall, opening the prosthetic valve 300 and allowing blood to flow in an antegrade direction 309.

Alternatively, a multicusp leaflet configuration may be utilized in the prosthetic valve 300, with the prosthetic valve having multiple leaflets configured in such a manner to allow the leaflets to co-apt within the lumen 308 of the support frame 310. The valve leaflets can have any suitable shape. Preferably, the valve leaflet includes one or more edges attached to a valve support frame 310 and extend within the lumen 308. The valve leaflets preferably have (n) edges and (n−1) edges of each valve leaflet preferably contact the support frame 310, where (n) is an integer equal to 2 or greater. Valve leaflets with (n) of 2, 3, or 4 are preferred, although leaflets with other shapes can also be used. Preferably, at least 2 edges of a valve leaflet are attached to a valve support frame 310, and at least one edge of a valve leaflet is a leaflet free edge that is not attached to any support frame.

A wide variety of materials acceptable for use as a valve member or valve leaflet are known in the art, and any suitable material can be utilized. The material chosen need only be able to perform as described herein, and be biocompatible, or able to be made biocompatible. Examples of suitable materials include natural materials, and synthetic materials.

In certain examples of the disclosure, the leaflet is formed from a flexible material comprising a naturally derived or synthetic collagenous material, and especially an extracellular collagen matrix material. Examples of suitable natural materials include collagen and extracellular matrix (ECM) material, such as submucosa. The "extracellular matrix" is typically a collagen-rich substance that is found in between cells in animal tissue and serves as a structural element in tissues. Such an extracellular matrix is preferably a complex mixture of polysaccharides and proteins secreted by cells. The extracellular matrix can be isolated and treated in a variety of ways. Following isolation and treatment, it is referred to as an ECM. ECM may be isolated from submucosa (including small intestine submucosa), stomach submucosa, urinary bladder submucosa, tissue mucosa, renal capsule, dura mater, liver basement membrane, pericardium or other tissues. One specific example of ECM is small intestine submucose (SIS). When implanted, SIS can undergo remodeling and can induce the growth of endogenous tissues upon implantation into a host. SIS has been used successfully in vascular grafts, urinary bladder and hernia repair, replacement and repair of tendons and ligaments, and dermal grafts. SIS is particularly well-suited for use as valve members, such as leaflets. Suitable extracellular matrix materials ("ECM material") include, for instance, submucosa (including, for example, small intestinal submucosa ("SIS"), stomach submucosa, urinary bladder submucosa, or uterine submucosa), renal capsule membrane, dura mater, pericardium, serosa, and peritoneum or basement membrane materials, including liver basement membrane. These layers may be isolated and used as intact natural sheet forms, or reconstituted collagen layers including collagen derived from these materials or other collagenous materials may be used. For additional information as to submucosa materials useful in the present disclosure, and their isolation and treatment, reference can be made to U.S. Pat. Nos. 4,902,508, 5,554,389, 5,993,844, 6,206,931, and 6,099,567, the contents of which are incorporated herein by reference. Renal capsule tissue can also be obtained from warm blooded vertebrates, as described more particularly in copending U.S. patent application Ser. No. 10/186,150, filed Jun. 28, 2002, and International Patent Application Serial Number PCT/US02/20499, filed Jun. 28, 2002, and published Jan. 9, 2003 as International Publication Number WO/03002165, the contents of which are incorporated herein by reference. In one example of the disclosure, the ECM material is porcine SIS. SIS can be prepared according to the method disclosed in U.S. 2004/0180042A1, published Sep. 16, 2004, the contents of which are incorporated herein by reference. In addition to xenogenic biomaterials, such as SIS, autologous tissue can be harvested as well. Additionally Elastin or Elastin Like Polypeptides (ELPs) and the like offer potential as a material to fabricate the flexible covering or discrete shaping members to form a device with exceptional biocompatibility. Another alternative is use of allographs such as harvested native valve tissue. Such tissue is commercially available in a cryopreserved state.

In one aspect, the valve member, and preferably a valve leaflet, is formed from explanted biological tissue, such as aortic tissue, that is treated in a manner that improves the biocompatibility of the tissue for an intended use. For example, the tissue may be treated to improve resistance to post-implantation mineralization. One preferred method is described in U.S. Pat. No. 5,595,571 (Filed Apr. 18, 1994), incorporated by reference herein in its entirety, which involves exposing biological material including cellular and non-cellular structural components to a buffered solution having a pH in the range from about 5.0 to about 8.0 and a temperature in the range from about 12.degree. C. to about 30.degree. C. for a sufficient amount of time to facilitate the degradation of cells by autolytic enzymes within the cells, whereby at least one region of the biological material is rendered substantially acellular while preserving the overall structural integrity and non-cellular structural components of the biological material The exposure occurs prior to any fixation of the biological material. Other suitable tissue treatments are described in the following references, all of which are incorporated herein by reference in their entirety: U.S. Pat. Nos. 5,720,777, 5,843,180 and 5,843,181 (Biological Material Pre-fixation Treatment); 4,798,611 (Enhancement of Xenogenic Tissue by treatment with glutaraldehyde and then irradiation); 4,813,958 (Crosslinked anisotropic mammalian diaphragm in surgical reconstruction); 3,966,401 (Tissue for Implantation so as to Provide Improved Flexibility by Tissue subjecting tissue to tanning fluid when under pressure until the tissue assumes a natural configuration during tanning in Tanning fluids including 4% formaldehyde and 2% glutaraldehyde); 4,800,603 (Tissue Fixation with Vapor by subjecting tissue to a vapor of a fixative while the tissue is unstressed); and 4,813,964 and 4,813,958 (Crosslinked anisotropic xenogenic diaphragm tissue in flexor tendon pulley reconstruction, such as a method of tissue replacement for nonfunctional flexor tendon pulleys including replacing the flexor tendon pulleys with anisotropic, crosslinked mammalian, bovine or porcine diaphragm which is characterized in that the diaphragm has one smooth side and one fibrous side, the smooth side being placed against the flexor tendon). Preferably, the explanted tissue explanted tissue is pre-treated by performing at least one of the following steps: maintaining the explanted tissue at a pH in the range from about 5.0 to about 8.0 and a temperature in the range from about 12.degree. C. to about 30.degree. C. for a sufficient amount of time sufficient to effect the degradation of at least a portion of the cells by autolytic enzymes within the cells; contacting the explanted tissue with a chemical cross-linking agent and then irradiating with X-ray or gamma radiation; contacting the explanted tissue with a tanning fluid including formaldehyde or glutaraldehyde; or placing tissue explanted tissue within an atmosphere of substantially unpressurized vapor of containing glutaraldehyde, and maintaining the tissue within the atmosphere of substantially unpressurized vapor in a manner sufficient to provide substantially uniform application of the fixative solution for a period of time to cause the desired fixation of said tissue.

The valve leaflet may be formed from a synthetic polymeric material. Examples of suitable polymeric materials include polyesters, such as poly(ethylene terephthalate), polylactide, polyglycolide and copolymers thereof; fluorinated polymers, such as polytetrafluoroethylene (PTFE), expanded PTFE and poly(vinylidene fluoride); polysiloxanes, including polydimethyl siloxane; and polyurethanes, including polyetherurethanes, polyurethane ureas, polyetherurethane ureas, polyurethanes containing carbonate linkages and polyurethanes containing siloxane segments. In addition, materials that are not inherently biocompatible may be subjected to surface modifications in order to render the materials biocompatible. Examples of surface modifications include graft polymerization of biocompatible polymers from the material surface, coating of the surface with a crosslinked biocompatible polymer, chemical modification with biocompatible functional groups, and immobilization of a compatibilizing agent such as heparin or other substances.

In addition, the valve leaflet material may be a biocompatible polyurethane or derivative thereof. One example of a biocompatible polyurethane is THORALON (THORATEC, Pleasanton, Calif.), as described in U.S. Pat. Application Publication No. 2002/0065552 A1 and U.S. Pat. No. 4,675,361, both of which are incorporated herein by reference. According to these patents, THORALON is a polyurethane base polymer (referred to as BPS-215) blended with a siloxane containing surface modifying additive (referred to as SMA-300). Base polymers containing urea linkages can also be used. The concentration of the surface modifying additive may be in the range of 0.5% to 5% by weight of the base polymer. The SMA-300 component (THORATEC) is a polyurethane comprising polydimethylsiloxane as a soft segment and the reaction product of diphenylmethane diisocyanate (MDI) and 1,4-butanediol as a hard segment. A process for synthesizing SMA-300 is described, for example, in U.S. Pat. Nos. 4,861,830 and 4,675,361, which are incorporated herein by reference. The BPS-215 component (THORATEC) is a segmented polyetherurethane urea containing a soft segment and a hard segment. The soft segment is made of polytetramethylene oxide (PTMO), and the hard segment is made from the reaction of 4,4'-diphenylmethane diisocyanate (MDI) and ethylene diamine (ED). THORALON can be manipulated to provide either porous or non-porous THORALON. Porous THORALON can be formed by mixing the polyetherurethane urea (BPS-215), the surface modifying additive (SMA-300) and a particulate substance in a solvent. The particulate may be any of a variety of different particulates or pore forming agents, including inorganic salts, which may be removed by contacting the material with a suitable solvent to dissolve and remove the inorganic salt after pore formation. Formation of porous THORALON is described, for example, in U.S. Pat. Nos. 6,752,826 and 2003/0149471 A1, both of which are incorporated herein by reference. Non-porous THORALON can be formed by mixing the polyetherurethane urea (BPS-215) and the surface modifying additive (SMA-300) in a suitable solvent, such as dimethyacetamide (DMAC). The composition can contain from about 5 wt % to about 40 wt % polymer, and different levels of polymer within the range can be used to fine tune the viscosity needed for a given process. The composition can contain less than 5 wt % polymer for some spray application examples. The entire composition can be cast as a sheet, or coated onto an article such as a mandrel or a mold to form a valve leaflet, which can be dried to remove the solvent.

Returning to the prosthetic valve 300 example described with respect to FIG. 4, the monocuspid valve member 350 or two or more valve leaflets may be securably mounted to the support frame 310 by any suitable means. The valve leaflet material can be attached to the support structure by any appropriate attachment means, including but not limited to, adhesive, fasteners, suturing, and tissue welding using heat and/or pressure. In one example, the valve member 350 or two or more valve leaflets is sutured to the longitudinal connecting members. Additionally, where the longitudinal connecting members are closely paired support members, the valve member or two or more valve leaflets may be sutured to both closely paired support members, thereby providing for redundancy in attaching the valve to the support frame 310.

Alternatively, the valve leaflet may be formed on the support structure by an appropriate means, including but not limited to vapor deposition, spraying, electrostatic deposition, ultrasonic deposition, or dipping. One or more valve leaflets can be attached to the support frame by other methods. In one example, a sheet of material is cut to form a valve leaflet and the edges of the leaflet are wrapped around portions of a support frame and portions of the valve leaflet sealably connected together to fasten the valve leaflet around the support frame. For example, one edge of a sheet of valve leaflet material can be wrapped around a portion of the support frame and held against the body of the valve leaflet, so that the valve leaflet material forms a lumen enclosing a portion of the support frame. A small amount of a suitable solvent is then applied to the edge of the valve leaflet material to dissolve the edge into an adjacent portion of the valve leaflet material and thereby seal the material around the support frame.

In another example, the sheet of valve leaflet material is shaped to form the valve leaflet that is attached to a portion of a support frame using stitching through the valve leaflet material and around a portion of the support structure, adhesives, tissue welding or cross linking to directly join the valve leaflet material to the support frame. A valve leaflet attached to a support frame can be permitted to move relative to the support frame, or the valve leaflet can be substantially fixed in its position or orientation with respect to the support frame by using attachment configurations that resist relative movement of the valve leaflet and the support frame.

Other prosthetic valves can be formed by attaching a means for regulating fluid flow, such as a valve leaflet or monocuspid valve member, to any support frame described according to the first example. One or more prosthetic valves can be implanted within a tubular body passage of a patient, especially a human, including for example in veins or arteries, to regulate fluid flow therein.

Methods of Delivery and Treatment

Artificial valve prostheses can be deployed at various locations and lumens in the body, such as, for example, coronary, vascular, nonvascular and peripheral vessels, ducts, and the like. In one example, a valve leaflet is attached to the support frame to provide an implantable valve prosthesis that can be implanted within a vein, for instance, near an incompetent venous valve to treat venous valve insufficiency. Prosthetic valve devices of the present disclosure are desirably adapted for deployment within the vascular system, and in certain preferred examples, are adapted for deployment within the venous system. Accordingly, a prosthetic valve can be adapted as a venous valve, for example, for attachment within veins of the legs or feet, to treat venous insufficiency.

The prosthetic valves described herein can be configured for delivery to a body vessel in a radially compressed configuration, and radially expanded at a point of treatment within the body vessel. The overall configuration, cross-sectional area, and length of a medical device frame having a tubular configuration (compressed or expanded) may depend on several factors, including the size and configuration of device, the size and configuration of the vessel in which the device will be implanted, the extent of contact between the device and the walls of the vessel, and the amount of retrograde flow through the vessel that is desired.

Preferably, the support frames and/or prosthetic valves described above can be radially intraluminally delivered inside the body by a catheter that supports the implantable frame in a compressed form as it is transported to the desired site, for example within a body vessel. Upon reaching the site, the implantable support frame can be expanded and securably placed within the body vessel, for example by securably engaging the walls of the body vessel lumen. The expansion mechanism may involve permitting the support frame to expand radially outward, for example, by inflation of a balloon formed in the distal portion of the catheter, to inelastically deform the frame and fix it at a predetermined expanded position in contact with the lumen wall. The expansion balloon can then be deflated and the catheter removed. In another technique, the implantable support frame is formed of a material that will self-expand after being compressed. During introduction into the body, the implantable support frame is restrained in the compressed condition. When the stent has been delivered to the desired site for implantation, the restraint is removed, allowing the implantable frame to self-expand by its own internal elastic restoring force. Once the implantable frame is located at the constricted portion of the lumen, the sheath is removed to expose the frame, which is expanded so it contacts the lumen wall. The catheter is subsequently removed from the body by pulling it in the proximal direction, through the larger lumen diameter created by the expanded prosthesis, which is left in the body.

Implantable frames or prostheses comprising the implantable frame can be delivered into a body lumen using a system which includes a catheter. An appropriately sized delivery catheter can be selected by one skilled in the art for a given application. For example, some examples can be delivered using a delivery catheter selected from one or more delivery catheter sizes from the group consisting of: 3, 4, 5, 6, 7, 8, 9, 10, 11, 12, 13, 14, 15, 16, 17, 18, 19, 20, 21, 22, 23, and 24 French (F) delivery catheters, or increments of 0.1 F therebetween. In some examples, a delivery catheter sized between 3 and 24 F, or preferably between about 6 F and 16 F can be used.

The implantable support frames and/or prosthetic valves can be placed in any medically appropriate location for a given application. For example, in some examples, the implantable frame can serve as part of a venous valve prosthetic and be implanted in the femoral vein, including at the proximal (groin), mid (mid section) or distal (adjacent to the knee) portions of the vein. Preferably, prosthetic valves are placed in the superficial venous system, such as the saphenous veins in the leg, or in the deep venous system, such as the femoral and popliteal veins extending along the back of the knee to the groin.

Methods of treatment preferably include the steps of loading a prosthetic valve in a radially compressed configuration into a delivery catheter, inserting the delivery catheter into a body vessel, translating the delivery catheter to a treatment site, deploying the artificial valve prosthesis by placing the artificial valve prosthesis in an expanded configuration at the treatment site to treat the subject, and withdrawing the delivery catheter from the body vessel.

Having described the disclosure in detail and by reference to specific examples thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure. It is therefore intended that the foregoing detailed description be regarded as illustrative rather than limiting, and that it be understood that it is the following claims, including all equivalents, that are intended to define the spirit and scope of this disclosure.

We claim:

1. A support frame suitable for prosthetic implantable valves comprising:
   a proximal annular member longitudinally spaced from a distal annular member axially aligned with the proximal annular member around a longitudinal axis;
   a plurality of longitudinal connecting members extending substantially parallel to the longitudinal axis from the proximal annular member to the distal annular member and defining a hypothetical circumferential plane around an outer surface of the support frame and defining a lumen extending from a proximal end to a distal end of the support frame around the longitudinal axis;
   the plurality of longitudinal connecting members including a first member opposably positioned across the lumen from a directly circumferentially adjacent second member without an intervening member disposed therebetween, a third member circumferentially adjacent to the first member, and a fourth member circumferentially adjacent to the third member;
   wherein a first circumferential distance is disposed between the first member and the second member, a second circumferential distance is disposed between the third member and the first member, and a third circumferential distance is disposed between the third member and the fourth member;
   wherein the first circumferential distance is greater than each of the second circumferential distance and the third circumferential distance; and
   wherein the circumferential distances are measured along the circumferential plane perpendicular to the longitudinal axis at a position between the proximal end and the distal end.

2. The frame of claim 1, wherein the fourth member is circumferentially adjacent to the second member;
   wherein a fourth circumferential distance is disposed between the fourth member and the second member;
   wherein the first circumferential distance is greater than the fourth circumferential distance;
   wherein the second circumferential distance between the first member and the third member is substantially equal to the fourth circumferential distance between the fourth member and the second member; and
   wherein the first circumferential distance between the first member and the second member is substantially equal to the sum of the second circumferential distance, the third circumferential distance, and the fourth circumferential distance.

3. The frame of claim 1, wherein the fourth member is circumferentially adjacent to the second member;
   wherein a fourth circumferential distance is disposed between the fourth member and the second member;
   wherein the first circumferential distance is greater than the fourth circumferential distance; and
   wherein the fourth circumferential distance between the fourth member and the second member is substantially equal to the third circumferential distance and one-half of the second circumferential distance.

4. The frame of claim 1, further comprising a fifth member circumferentially adjacent to the fourth member and the second member;
wherein a fourth circumferential distance is disposed between the fourth member and the fifth member;
wherein a fifth circumferential distance is disposed between the fifth member and the second member;
wherein the first circumferential distance is greater than the fourth circumferential distance; and
wherein the first circumferential distance is greater than the fifth circumferential distance.

5. The frame of claim 4, wherein the second circumferential distance is substantially equal to the fifth circumferential distance; and
wherein the third circumferential distance is substantially equal to the fourth circumferential distance.

6. The frame of claim 5, wherein the first circumferential distance between the first member and the second member is substantially equal to the sum of the third circumferential distance and the fourth circumferential distance.

7. The frame of claim 1, further comprising a valve member attached to the support frame and moveable within the lumen to regulate fluid flow therein, where the valve member is attached to the first member and is moveable across the lumen between an open position permitting fluid flow through the lumen from the proximal end to the distal end, and a closed position substantially preventing fluid flow through the lumen, the valve member contacting the circumferential plane between the first member and the second member in the closed position.

8. A support frame suitable for prosthetic implantable valves comprising:
a proximal annular member longitudinally spaced from a distal annular member axially aligned with the proximal annular member around a longitudinal axis;
a plurality of longitudinal connecting members extending substantially parallel to the longitudinal axis from the proximal annular member to the distal annular member and defining a hypothetical circumferential plane around an outer surface of the support frame and defining a lumen extending from a proximal end to a distal end of the support frame around the longitudinal axis;
the plurality of longitudinal connecting members including a first member opposably positioned across the lumen from a directly circumferentially adjacent second member without an intervening member disposed therebetween, a third member circumferentially adjacent to the first member, a fourth member circumferentially adjacent to the third member, and a fifth member circumferentially adjacent to the fourth member and the second member;
wherein a first circumferential distance is disposed between the first member and the second member, a second circumferential distance is disposed between the third member and the first member, a third circumferential distance is disposed between the third member and the fourth member, a fourth circumferential distance is disposed between the fourth member and the fifth member, and a fifth circumferential distance is disposed between the fifth member and the second member;
wherein the first circumferential distance is greater than each of the second circumferential distance, the third circumferential distance, the fourth circumferential distance, and the fifth circumferential distance; and
wherein the circumferential distances are measured along the circumferential plane perpendicular to the longitudinal axis at a position between the proximal end and the distal end.

9. The frame of claim 8, wherein the second circumferential distance is substantially equal to the fifth circumferential distance; and
wherein the third circumferential distance is substantially equal to the fourth circumferential distance.

10. The frame of claim 9, wherein the first circumferential distance between the first member and the second member is substantially equal to the sum of the third circumferential distance and the fourth circumferential distance.

11. The frame of claim 8, wherein the second circumferential distance between the first member and the third member is less than about 10% of the longitudinal length of the members; and
wherein the fifth circumferential distance between the fifth member and the second member is less than about 10% of the longitudinal length of the members.

12. The frame of claim 8, wherein a radial angle of about $(2\pi/4)$ radians is subtended by the sum of the third circumferential distance and one half of the second circumferential distance.

13. The frame of claim 8, wherein a radial angle of about $(2\pi/2)$ radians is subtended by the sum of the first circumferential distance, one half of the second circumferential distance, and one half of the fifth circumferential distance.

14. The frame of claim 8, further comprising a valve member attached to the support frame and moveable within the lumen to regulate fluid flow therein, where the valve member is attached to the first member and is moveable across the lumen between an open position permitting fluid flow through the lumen from the proximal end to the distal end, and a closed position substantially preventing fluid flow through the lumen, the valve member contacting the circumferential plane between the first member and the second member in the closed position.

15. A support frame suitable for prosthetic implantable valves comprising:
a proximal annular member longitudinally spaced from a distal annular member axially aligned with the proximal annular member around a longitudinal axis;
a plurality of longitudinal connecting members extending substantially parallel to the longitudinal axis from the proximal annular member to the distal annular member and defining a hypothetical circumferential plane around an outer surface of the support frame and defining a lumen extending from a proximal end to a distal end of the support frame around the longitudinal axis;
the plurality of longitudinal connecting members including a first member opposably positioned across the lumen from a directly circumferentially adjacent second member without an intervening member disposed therebetween, a third member circumferentially adjacent to the first member, a fourth member circumferentially adjacent to the third member, and a fifth member circumferentially adjacent to the fourth member and the second member;
wherein a first circumferential distance is disposed between the first member and the second member, a second circumferential distance is disposed between the third member and the first member, a third circumferential distance is disposed between the third member and the fourth member, a fourth circumferential distance is disposed between the fourth member and the fifth member, and a fifth circumferential distance is disposed between the fifth member and the second member;

wherein the first circumferential distance is greater than each of the second circumferential distance, the third circumferential distance, the fourth circumferential distance, and the fifth circumferential distance;

wherein the second circumferential distance is substantially equal to the fifth circumferential distance;

wherein the third circumferential distance is substantially equal to the fourth circumferential distance; and wherein the circumferential distances are measured along the circumferential plane perpendicular to the longitudinal axis at a position between the proximal end and the distal end.

16. The frame of claim 15, wherein the first circumferential distance between the first member and the second member is substantially equal to the sum of the third circumferential distance and the fourth circumferential distance.

17. The frame of claim 15, wherein the second circumferential distance between the first member and the third member is less than about 10% of the longitudinal length of the members; and wherein the fifth circumferential distance between the fifth member and the second member is less than about 10% of the longitudinal length of the members.

18. The frame of claim 15, wherein a radial angle of about $(2\pi/4)$ radians is subtended by the sum of the third circumferential distance and one half of the second circumferential distance.

19. The frame of claim 15, wherein a radial angle of about $(2\pi/2)$ radians is subtended by the sum of the first circumferential distance, one half of the second circumferential distance, and one half of the fifth circumferential distance.

20. The frame of claim 15, further comprising a valve member attached to the support frame and moveable within the lumen to regulate fluid flow therein, where the valve member is attached to the first member and is moveable across the lumen between an open position permitting fluid flow through the lumen from the proximal end to the distal end, and a closed position substantially preventing fluid flow through the lumen, the valve member contacting the circumferential plane between the first member and the second member in the closed position.

* * * * *